US008709498B2

(12) United States Patent
     Mainnemare

(10) Patent No.: US 8,709,498 B2
(45) Date of Patent: *Apr. 29, 2014

(54) METHOD OF STIMULATING TISSUE HEALING

(76) Inventor: Arnaud Mainnemare, Neville (FR)

(*) Notice: Subject to any disclaimer, the term of this patent is extended or adjusted under 35 U.S.C. 154(b) by 371 days.

This patent is subject to a terminal disclaimer.

(21) Appl. No.: 12/976,414

(22) Filed: Dec. 22, 2010

(65) Prior Publication Data

US 2011/0091578 A1    Apr. 21, 2011

Related U.S. Application Data

(60) Division of application No. 12/236,613, filed on Sep. 24, 2008, now Pat. No. 7,879,366, which is a division of application No. 10/622,262, filed on Jul. 18, 2003, now abandoned, which is a continuation of application No. PCT/FR02/00151, filed on Jan. 16, 2002.

(30) Foreign Application Priority Data

Jan. 23, 2001  (FR) ..................................... 01 00862

(51) Int. Cl.
     *A61K 33/14*         (2006.01)
(52) U.S. Cl.
     USPC ......................................................... 424/665
(58) Field of Classification Search
     USPC ......................................................... 424/665
     See application file for complete search history.

(56) References Cited

U.S. PATENT DOCUMENTS

| 3,998,945 A | 12/1976 | Vit |
| 4,012,842 A * | 3/1977 | Vit ................................ 433/216 |
| 7,879,366 B2 * | 2/2011 | Mainnemare ................. 424/665 |

FOREIGN PATENT DOCUMENTS

| DE | 40 41 703 A1 | 7/1992 |
| DE | 197 12 565 A1 | 10/1998 |
| DE | 198 16 102 C1 | 9/1999 |
| JP | 49-48846 | 5/1974 |
| JP | 07-206609 A | 8/1995 |
| JP | 11-279057 | 10/1999 |
| WO | 00/74743 A1 | 12/2000 |

OTHER PUBLICATIONS

Killoy Chemical treatment of periodontitis: local delivery of antimicrobials. International dental journal Jun. 1998 vol. 48 No. 3 Suppl.1 pp. 305-315 abstract.*
Kulaev et al. Influence of sodium hypochlorite on oxygen blance and function of small intestine in experimental peritonitis Byulleten Eksperimental'noi Biologii i Meditsiny (1991), 112(7), 65-7.*
Sally F. Bloomfield et al., "The Antibacterial Properties of Sodium Dichloroiso-cyanurate and Sodium Hypochlorite Formulations," J. Appl. Bacteriol., 1979, vol. 46, pp. 65-73.
André M. Cantin, "Taurine Modulation of Hypochlorous Acid-induced Lung Epithelial Cell Injury in Vitro—Role of Anion Transport," J. Clin. Invest., Feb. 1994, vol. 93, pp. 606-614.
Cecil Testbook of Medicine, 21st Edition, 2000, pp. 1810-1814.
Noel Claffey et al., "An Overview of Nonsurgical and Surgical Therapy," Periodontology 2000, 2004, vol. 36, pp. 35-44.
Contreras et al., "Human herpesviridae in acute necrotizing ulcerative gingivitis in children in Nigeria," Oral Microbiology and Immunology, 1997, vol. 12, No. 5, pp. 259-265, ISSN: 0902-0055.
Joanna M.S. Davies et al., "Inhibition of Colleagenase Activity by N-Chlorotaurine, a Product of Activated Neutrophils," Arthritis Rheum., Mar. 1994, vol. 37, No. 3, pp. 424-427.
Douglas R. Dixon et al., "Modulation of the Innate Immune Response within the Periodontium," Periodontology 2000, 2004, vol. 35, pp. 53-74.
Kurt Fuursted et al., "Evaluation of Bactericidal Activity and Lag of Regrowth (Postantibiotic Effect) of Five Antiseptics on Nine Bacterial Pathogens," J. of Antimicrobial Chemo., 1997, vol. 40, pp. 221-226.
Erica Gemmel et al., "Immunoregulatory Control of Th1/Th2 Cytokine Profiles in Periodontal Disease," Periodontology 2000, 2004, vol. 35, pp. 21-41.
Matthew B. Grisham et al., "Chlorination of Endogenous Amines by Isolated Neutrophils," J. Biol. Chem., Aug. 25, 1984, vol. 259, No. 16, pp. 10404-10413.
Ronald E. Hand et al., "Analysis of the Effect of Dilution on the Necrotic Tissue Dissolution Property of Sodium Hypochlorite," J. Endod., Feb. 1978, vol. 4, No. 2, pp. 60-64.
J.P. Heggers et al., "Bactericidal and Wound-Healing Properties of Sodium Hypochlorite Solutions: The 1991 Lindberg Award," J. Burn Care Rehabil., 1991, vol. 12, pp. 420-424.
Eduard Hidalgo et al., "Growth-Altering Effects of Sodium Hypochlorite in Cultured Human Dermal Fibroblasts," Life Sci., 2000, vol. 67, pp. 1331-1344.
Ryan J. Huxtable, "Sources and Turnover Rates of Taurine in Nursing and Weaned Rat Pups," J. Nutr., 1981, vol. 111, pp. 1275-1286.
Julich et al., "On the Virucidal efficacy of chemical and physical disinfectants or disinfection procedures," Hyg. Med., 1993, vol. 18, pp. 303-326.
Chaekyun Kim et al., "The Production of Superoxide Anion and Nitric Oxide by Cultured Murine Leukocytes and the Accumulation of TNF-α in the Conditioned Media Is Inhibited by Taurine Chloramine," Immunopharmacology, 1996, vol. 34, pp. 89-95.
C. Kim et al., "Uptake of Taurine and Taurine Chloramine in Murine Macrophages and Their Distribution in Mice with Experimental Inflammation," Adv. Exp. Med. Bio., 1998, vol. 442, pp. 169-176.
Keiko Kiuchi et al., "Microbicides Containing Nitrogen-Containing Halogen Compounds," Chemical Abstracts, retrieved from STN, Database Accession No. 123:278710.
Joseph A. Knight, "Review: Free Radicals, Antioxidants, and the Immune System," Annals of Clinical of Laboratory Science, 2000, vol. 30, No. 2, pp. 145-158.

(Continued)

*Primary Examiner* — Jennifer M Kim
(74) *Attorney, Agent, or Firm* — DLA Piper LLP (US)

(57) ABSTRACT

A method of stimulating tissue healing in humans or animals includes administering to a human or animal suffering from lesions and infections linked to chronic and/or acute periodontitis a pharmaceutically effective amount of a pharmaceutical composition including (i) at least one sodium halopohalite, and (ii) at least one N-halogenated taurine, wherein halogens from the (i) at least one sodium halopohalite and from the (ii) at least one N-haloamine taurine, which may be the same or different, are selected from the group consisting of fluorine, iodine, bromine and chlorine.

6 Claims, No Drawings

(56) References Cited

OTHER PUBLICATIONS

Ewa Kontny et al., "Taurine Chloramine Inhibition of Cell Proliferation and Cytokine Production by Rheumatoid Arthritis Fibroblast-Like Synoviocytes," Arthritis & Rheumatism, Dec. 1999, vol. 42, No. 12, pp. 2552-2560.

E. Kontny et al., :The Mechanism of Taurine Chloramine Inhibition of Cytokine (Interleukin-6, Interleukin-8) Production by Rheumatoid Arthritis Fibroblast-Like Synoviocytes, Arthritis and Rheumatism, 2000, vol. 43, No. 10, pp. 2169-2177.

Charles Kunsch et al., "Oxidative Stress as a Regulator of Gene Expression in the Vasculature," Circ. Res., 1999, vol. 85, pp. 753-766.

A.D. Lelianov et al., "The Use of an Electrolytic Solution of Sodium Hypochlorite in Acute Suppurative Diseases of the Soft Tissues," Klin Khir., 1991, Russian (translation only, one page).

Y. Liu et al., "Taurine Chloramine Inhibits Production of Nitric Oxide and Prostaglandin $E_2$ in Activated C6 Glioma Cells by Suppressing Inducible Nitric Oxide Synthase and Cyclooxygenase-2 Expression," Molecular Brain Research, 1998, vol. 59, pp. 189-195.

Yong Liu et al., "Monocyte Chemoattractant Protein-1 and Macrophage Inflammatory Protein-2 Production Is Inhibited by Taurine Chloramine in Rat C6 Glioma Cells," Immunology Letters, 1999, vol. 70, pp. 9-14.

Z.X. Liu et al., "Negative Chemotaxis in Cytophaga Johnsonae," Canadian Journal of Microbiology, May 1996, vol. 42, No. 5, pp. 515-518.

A. Mainnemare et al., "Hypochlorous Acid and Taurine-N-Monochloramine in Periodontal Diseases," J. Dent. Res., 2004, vol. 83, No. 11, pp. 823-831.

David Male et al., "Advanced Immunology," J.B. Lippincott Company, Philadelphia, 2nd Edition, 1989, vol. 5, pp. 1-15.

V.V. Malinovskaya et al., "Immune Homeostasis and Interferon Status of Newborns from Mothers with Cytomegalovirus and Herpes Simplex Virus Infections," Russ J. Immunolo, Jul. 2000, vol. 5, No. 2, pp. 177-184 (translation—one page only).

J. Marcinkiewicz et al., "Differential Effects of Chlorination of Bacteria on their Capacity to Generate NO, TNF-α and IL-6 in Macrophages," Immunology, 1994, vol. 83, pp. 611-616.

Janusz Markinkiewicz et al., "Taurine Chloramine, a Product of Activated Neutrophils, Inhibits in Vitro the Generation of Nitric Oxide and Other Macrophage Inflammatory Mediators," J. of Leukoeyte Biology, Dec. 1995, vol. 58, pp. 667-674.

Janucz Marcinkiewicz, "Regulation of Cytokine Production by Eicosanoids and Nitric Oxide," Arch. Immunol. Ther. Exp., 1997, vol. 45, pp. 163-167.

Janusz Marcinkiewicz, "Neutrophil Chloramines: Missing Links between Innate and Acquired Immunity," Immuno. Today, Decmeber 1997, vol. 18, No. 12, pp. 577-580.

Janusz Marcinkiewicz, "Nitric Oxide and Antimicrobial Acitivyt of Reactive Oxygen Intermediates," Immunopharm., 1997, vol. 37, pp. 35-41.

J. Marcinkiewicz et al., "Modulation of Antigen-Specific T-cell Activation in vitro by Taurine Chloramine," Immunology, 1998, vol. 94, pp. 325-330.

Janusz Marcinkiewicz et al., "Taurine Chloramine Down-Regulates the Generation of Murine Neutrophil Inflammatory Mediators," Immunopharm., 1998, vol. 40, pp. 27-38.

J. Marcinkiewicz et al., "Regulation of Murine Dendritic Cell Functions in vitro by Taurine Chloramine, a Major Product of the Neutrophil Myeloperoxidase-Halide System," Immunology, 1999, vol. 98, pp. 371-378.

J. Marcinkiewicz et al., "Antimicrobial and Cytotosic Acitvity of Hypochlorous Acid: Interactions with Taurine and Nitrite," Inflamm. Res., 2000, vol. 49, pp. 280-289.

Leah A. Marquez et al., "Chlorination of Taurine by Myeloperoxidase," The Journal of Biological Chemistry, Mar. 1994, vol. 269, No. 11, pp. 7950-7956.

Martindale—The Complete Drug Reference, "Disinfectants and Preservatives," The Pharmaceutical Press, 32nd Edition, London, UK, 1999, p. 1124, col. 3.

Scott Masten et al., "Chloramine-T [127-65-1] and Metabolite p-Toluenesulfonamide [70-55-3]: Review of Toxicological Literature," Toxicological Literature, Feb. 2002, pp. Cover—6.

Bruno Megarbane et al., "Cytokines du Système de Défense: Interleukines et Chimiokines," Medecine Therapeutique, vol. 4, No. 8, pp. 641-653, and English translation.

Jeanne Meyers et al., "Preparation and Chemical Characterization of Radioiodinated Bleomycin," Journal of Nuclear Medicine, 1975, vol. 16, No. 9, pp. 835-838.

Ketil Moen et al., "Immunoglobulin G and A Antibody Responses to *Bacteroides forsythus* and *Prevotella intermedia* in Sera and Synovial Fluids of Arthritis Patients," Clin. and Diag. Lab. Immuno., Nov. 2003, pp. 1043-1050.

Thomas Moeslinger et al., "Inhibition of Inducible Nitric Oxide Synthesis by Oxidized Lipoprotein(a) in a Murine Macrophage Cell Line," FEBS Letters, 2000, vol. 478, pp. 95-99.

Nagl et al., "Activity of N-chlorotaurine against herpes simplex and adenoviruses," Antiviral Research, 1998, vol. 38, pp. 25-30.

William F. Owen, Jr. et al., "Synthesis and Release of Leukotriene $C_4$ by Human Eosinophls[1]," The Journal of Immunology, Jan. 15, 1987, vol. 138, No. 2, pp. 532-538.

Eunkyue Park et al., "Taurine Chloramine Inhibits the Synthesis of Nitric Oxide and the Release of Tumor Necrosis Factor in Activated RAW 264.7 Cells," Journal of Leukocyte Biology, Aug. 1993, vol. 54, pp. 119-124.

Eunkyue Park et al., "Preactivation Exposure of RAW 264.7 Cells to Taurine Chloramine Attenuates Subsequent Production of Nitric Oxide and Expression of iNOS mRNA," Journal of Leukocyte Biology, Feb. 1997, vol. 61, pp. 161-166.

Juliet M. Pullar et al., "Loss of GSH and Thiol Enzymes in Endothelial Cells Exposed to Sublethal Concentrations of Hypochlorous Acid," The American Physiological Society, Oct. 1999, vol. 4, Pt. 2, pp. H1505-H1512.

Michael R. Quinn et al., "Taurine Chloramine Inhibits Prostaglandin $E_2$ Production in Activated Raw 264.7 Cells by Post-Transcriptional Effects on Inducible Cyclooxygenase Expression," Immunology Letters, 1996, vol. 50, pp. 185-188.

Juan Jose Segura et al., "Comparative Effects of Two Endodontic Irrigants, Chlorhexidine Digluconate and Sodium Hypochlorite, on Macrophage Adhesion to Plastic Surfaces," Journal of Endodontics, Apr. 1999, vol. 25, No. 4, pp. 243-246.

Chandan K. Sen et al., "Antioxidant and Redox Regulation of Gene Transcription," The FASEB Journal, May 1996, vol. 10, pp. 709-720.

Gregory J. Seymour et al., "Shouts and Whispers: an Introduction to Immunoregulation in Periodontal Disease," Periodontology 2000, 2004, vol. 35, pp. 9-13.

Ming Shih et al., "The Bactericidal Efficiency of Sodium Hypochlorite as an Endodontic Irrigant," Oral. Surg., Apr. 1970, vol. 29, No. 4, pp. 613-619.

T.W. Stief et al., "Siglet Oxygen Inhibits Agonist-Induced P-Selectin Expression and Formation of Platelet Aggregates," Clinical and Applied Thrombosis/Hemostasis, 2001, vol. 7, No. 3, pp. 219-224.

Tetsuya Tatsumi et al., "Hypochlorous Acid and Chloramines Increase Endothelial Permeability: Possible Involvement of Cellular Zinc," The American Physiological Society, Oct. 1994, vol. 4, Pt. 2, pp. H1597-H1607.

S.D. The, "The Solvent Action of Sodium Hypochlorite on Fixed and Unfixed Necrotic Tissue," Oral Surg., Jun. 1979, vol. 47, No. 6 pp. 558-561.

Glenn F. Vile et al., "Initiation of Rapid, P53-Dependent Growth Arrest in Cultured Human Skin Fibroblasts by Reactive Chlorine Species," Archives of Biochemistry and Biophysics, May 1, 2000, vol. 377, No. 1, pp. 122-128.

Margaret C.M. Vissers et al., "Hypochlorous Acid Causes Caspase Activation and Apoptosis or Growth Arrest in Human Endothelial Cells," Biochem. J., 1999, vol. 344, pp. 443-449.

Walter Vogt, "Complement Activation by Myeloperoxidase Products Released from Stimulated Human Polymorphonuclear Leukocytes," Immunobiol., 1996, vol. 195, pp. 334-346.

(56) References Cited

OTHER PUBLICATIONS

Charles E. Wright et al., "Taurine: Biological Update," Ann. Rev. Biohcem., 1986, vol. 55, pp. 427-453.

J.M. Zgliczynski et al., "Chloramines as Intermediates of Oxidation Reaction of Amino Acids by Myeloperoxidase," Biochem. Biophys. Acta., 1971, vol. 235, pp. 419-424.

Y. Ono et al., "Synthesis and Characterization of Vitamin $D_3$ Derivatives Having Hydroxyl Group at Postion 1β," Chugai Pharmaceutial Co. and Kobe Women's College of Pharmacy, *Speech Collection of the 114th Annual Meeting of the Pharmaceutical Society of Japan*, 1994, p. 292, 3 pages containing original Japanese summary and 6 pages of English translation (abstract of lecture).

\* cited by examiner

METHOD OF STIMULATING TISSUE HEALING

RELATED APPLICATIONS

This is a divisional of U.S. Ser. No. 12/236,613, filed Sep. 24, 2008, which is a divisional of U.S. Ser. No. 10/622,262, filed Jul. 18, 2003, which is a continuation of International Application No. PCT/FR02/00151, with an international filing date of Jan. 16, 2002, which is based on French Patent Application No. 01/00862, filed Jan. 23, 2001.

TECHNICAL FIELD

This disclosure relates a new composition containing halogenated compounds for (1) the treatment of viral, bacterial, parasitical, fungal infections, or infections generated from non-conventional transmissible agents; (2) the treatment of chronic, progressive or acute inflammation; (3) immunomodulator treatments, and/or tissue healing stimulator treatments; and (4) pre- and/or per- and/or post-surgical irrigations. The composition is particularly helpful as a local use antiseptic. The disclosure also relates to a method of stimulating tissue healing.

BACKGROUND

1. The Hypochlorite of Alkaline Metal.

Hypochlorite of alkaline metal and, particularly, the sodium hypochlorite (NaOCl), has been used since the 19$^{th}$ century for its antiseptic properties. Alkaline metal hypochlorite is an alkaline metal salt of hypochlorous acid. The available chloride level of sodium hypochlorite solutions is equal to the addition of HOCl (hypochlorous acid) and OCl$^-$ (hypochlorous anion) concentrations (Bloomfield & Miles, 1979). The hypochlorite active form, i.e., the hypochlorous acid, is a highly strong oxidant that plays a role in the mammalian defense system. HOCl is synthesized in polymorphonuclear neutrophils and monocytes (Wright et al., 1986) during the respiratory burst by the myeloperoxidase-$H_2O_2$-halide system. Hypochlorous acid is unstable and reacts readily with primary and secondary amines to generate various N-chloramines (Zgliczynski et al., 1971).

In polymorphonuclear cytosol, an amino acid (i.e. taurine) is particularly abundant and has a very high reactivity with hypochlorous acid to yield the taurine N-chloramine (TauCl). This chloramine is less toxic and reactive than hypochlorous acid. In addition, TauCl is the most stable of the chloramines (Zgliczynski et al., 1971; Marquez & Dunford, 1994). Moreover, taurine seems to have a high protective role in both intra- and extracellular environments, via its high scavenger activity with hypochlorous acid (Cantin, 1994; J. Marcinkiewicz et al., 1998). However, long-lived taurine N-chloramines can move and react (i.e., oxidize and/or chlorinate) at distance from their formation to generate tissue damage (Zgliczynski et al., 1971).

At the physiological pH (7.4), taurine and hypochlorous acid react spontaneously and with a 1/1-molecule stoechimetry to yield a taurine N-monochloramine. At acidic pH, this reaction generates both taurine N-monochloramines and taurine (N,N)-dichloramines. Taurine and, particularly, nitrites ($NO_2^-$), compete with other antioxidants to scavenge hypochlorous acid in the extracellular medium. Their concentrations are roughly equal. Thus, the main hypochlorous acid scavengers are nitrites, which react together to yield a lesser toxic derivative than TauCl. In the polymorphonuclear neutrophil cytosol, due to its high concentration (≈20 mM), taurine is the main scavenger of hypochlorous acid (J. Marcinkiewicz, 2000).

2. Sodium Hypochlorite, Hypochlorous Acid, N-Chloramine Properties.

a. Dissolving Tissue Abilities.

In aqueous solution, the sodium hypochlorite (NaOCl) is well known to be caustic. It is a non-specific agent able to hydrolyze necrotic tissues. This property is due to the presence of sodium hydroxide (NaOH). The tissue dissolving level (e.g. mainly necrotic tissues) is in accordance with NaOCl concentration, contact surface (Hand et al., 1978), contact time and NaOCl solution amount used (The et al., 1979).

Thus, even if a NaOCl concentration lower than 0.5% is not good enough to totally dissolve necrotic tissues, the reduced toxicity of these low concentrations is interesting. However, this decreased ability to dissolve necrotic tissues may be made up for by a NaOCl temperature increased to 37° C., even if at this temperature, the NaOCl stability is below 24 hours.

b. HOCl and Taurine N-Monochloramine Stability in Aqueous Solution.

Sodium hypochlorite (NaOCl):

Sodium hypochlorite is a highly unstable molecule. At levels below 5 g/l of available chlorine, its stability is under 2 weeks and depends on the following factors:

Light: Sodium hypochlorite is highly sensitive to light and should be protected by suitable packaging.

Temperature: NaOCl is highly sensitive to temperature greater than 30° C.

Presence of metal or organic matter: hypochlorite aqueous solution (containing HOCl molecules) (i.e.: NaOCl+$H_2O$ ⇔ HOCl+NaOH) is neutralized by organic matter. Hypochlorite solution is efficient both when it can act readily and when it is in excess in comparison to an organic matter amount.

pH value: EP 0471129 A1 has established that a pH value between 10 and 10.5 yields a high stability to NaOCl oxidative activity (greater than 24 months).

Taurine N-Chloramine:

At a physiological pH (7.4) and at 37° C., the taurine N-chloramine is the more stable of the chloramines (the oxidative activity decrease is below 5%/hour at 37° C.) (Grisham M B, Jefferson M M, Melton D F, Thomas E L—J. Biol. Chem. 1984; 259: 10404-13). However, in aqueous solution, the solubility of taurine N-chloramine sodium salt with a pH value between 7 and 8 is greater, but has a lower stability of its oxidative activities (DE 4041703 A1), and at a pH=8.3, the stability decreases by around 30% in 15 days followed by a decrease of around 0.71% per day (i.e. this equals a decrease of around 61% in 65 days).

c. Cell Toxicity and Viability.

Cell toxicity results mainly from an intracellular protein loss, which generates both an adherence decrease to substrates and cell deformation.

Cell viability alteration results mainly from the irreversible decrease of mitochondrial activity and therefore, a reduction of energy generated by cell respiratory.

The vulnerability of different cell organisms to NaOCl and TauCl depends on many factors:

The exposition level of the cell surface. Thus, cell systems with a high cell organization e.g. in epithelium and dental plaque are less sensitive (i.e. surface cells are sacrificed for profound cells) than one-cell systems (prokaryotes, mammalian mobile cells, or other one-cell systems).

Membrane type that protects intracellular elements (i.e. membrane permeability level to oxidants). The most efficient are viral proteinic membranes.

A membrane presence that protects key intracellular systems (e.g., DNA (nucleus), energetic production (mitochondria), secretion process (Golgi's apparatus), etc.). Prokaryotes do not possess these protector systems and, consequently, are more vulnerable.

The intracellular antioxidant amount (i.e., gluthatione, acetyl N-cysteine, taurine, amino acids, thiol groups, etc.) that is specific for each cell type. Prokaryotes possess a down antioxidant level.

The extracellular antioxidant amount (i.e. taurine, thiol groups, organic matter, metal, blood, extracellular matrix, etc.).

The liquid flux level that irrigates cells and, consequently, dilutes oxidants.

The exposition time to oxidants.

The local physicochemical environment (e.g. surface-active, oxidants, olfactory or gustatory properties, pH, pKa, density, solubility, viscosity, coloration, water-ectanol sharing factor).

In a therapeutic treatment in vivo, the factors described above should be integrated for the determination of active agent levels to adapt them to both clinic status and therapeutic aims.

i) Sodium Hypochlorite (NaOCl) or Hypochlorous Acid (HOCl):

On the rat macrophage like-cells RAW 264.7, with a (NaOCl)=1 mM (NaOCl concentration), the cell viability is highly altered (irreversible)(Park E. et al., 1997).

On the mouse macrophages, with (HOCl)>0.125 mM, cell death increases significantly. This toxicity is abolished by a nitrite ($NO_2$) excess ($NO_2^-$ alone does not generate cytotoxic activity) (Marcinkiewicz J. et al., 2000).

On human macrophages, fibroblasts and keratinocytes, in vitro:
  With (NaOCl)=13.433 mM, toxicity is so great that it cannot be neutralized by antioxidants (i.e. with physiological concentrations).
  With (NaOCl)>6.7165 mM, NaOCl has a high toxicity.
  With (NaOCl)<3.358 mM, toxicity can be neutralized by an antioxidant addition.
  With (NaOCl)<1.679 mM, toxicity is very low with an antioxidant presence (Hidalgo E. & Dominguez C., 2000).

The adherence loss of macrophages generated by HOCl:
  With (NaOCl)=1.0075 mM, after two hours of contact in vitro, 95% of the cells are alive but only 40% keep their adherence to substrates.

On human endothelial cells in vitro (Pullar J M et al., 1999):
  With [HOCl]≤25 µM, HOCl is not toxic.
  With [HOCl]>25 µM, cell toxicity increases progressively (exposition time-dependent).
  With [HOCl]=50 µM, some cell contractions were observed, the cells became rounded within the first 10 minutes and some lost their adherence after one hour and the majority after three hours.

On human fibroblasts in vitro:
  With (NaOCl)≥1,0075 mM (observed for 24 hours after a 15-minute exposition) cell viability is altered.
  With (NaOCl)=16,791 mmol/l cell morbidity is complete.
  For 67,165 µmol/l<(NaOCl)<671,655 µmol/l, 100% of cells are alive.
  With (NaOCl)<671,655 µmol/l, and a FCS presence (2%), cell viability is not altered (24 hours of exposure) and both growth and cell proliferation are stimulated (the latter enhance with the (NaOCl) decrease and with a highest efficiency at 33,582 µmol/l) (Hidalgo E. & Dominguez C., Life Sci. 2000 Aug. 4; 67(11):1331-44).
  With (HOCl)<50 µM, HOCl does not alter in vitro human fibroblast skin viability and does not induce cell apoptose (Vile G. F. et al., 2000).

ii) The Effects of Taurine N-Chloramine (TauCl) on Cell Viability:

On rat C6 glioma cells, a (TauCl)=0~2 mM does not alter cell viability in vitro (Liu Y. et al., 1999).

On human skin fibroblasts, a (TauCl)≤100 µM does not induce cytotoxicity or cell apoptose in vitro (Vile G. F. et al., 2000).

On human synoviocytes-like fibroblastes, with (TauCl)= 400-500 µM, cell morphology changes (~30%-50% of cells took a rounded form and lost their adherence to the plastic surfaces) although viability has been preserved (≥95%) (Kontny E. et al., 1999).

On mouse T cells:
  With (TauCl)=30-300 µM, cell viability is not altered (i.e. mitochondrial activity).
  At 300 µM, TauCl is cytotoxic (Marcinkiewicz J. et al., 1998).

On mouse dendritic cells incubated 24 hours with TauCl:
  For 0.05 mM<(TauCl)<0.5 mM, mitochondrial activity (cell viability) is not altered.
  With (TauCl)>0.5 mM, cell viability decrease significantly (Marcinkiewicz J. et al., 1999).

On macrophages or macrophage-line cells, with a (TauCl)= 50~600 µM, cell viability is not altered. (TauCl)>1 mM alters it (Marcinkiewicz J. et al., 1995).

d. Cellular Take-Up of Exogenous HOCl and Taurine N-Chloramine.

HOCl is a lipophilic oxidant and, consequently, easily and readily cross cell membranes (i.e. ~80% of HOCl molecules are taken up by human fibroblasts within the first 10 minutes) (Vile G. F. et al., 2000). In vitro with (HOCl)=35 µM, endothelial cells take up 50% of HOCl molecules within ½ minute and 100% within 15 minutes, with a high majority within the first 10 minutes (Pullar J. M. et al., Am J Physiol. 1999 October; 277 (4 Pt 2): H1505-12).

TauCl is taken up by specific transport systems. Therefore, in vitro, the $K_m$ and the $V_{max}$ values in relaxed rat RAW264.7 cells are 23.3 µM and 51.3 pmol/min/$10^6$ cells, respectively ($K_m$=28.1 µM and $V_{max}$=90.9 pmol/min/$10^6$ cells for taurine).

In LPS-stimulated macrophages, $K_m$=45.9 µM and $V_{max}$=82.6 pmol/min/$10^6$ cells for TauCl, and $K_m$=17.3 µM and $V_{max}$=116.3 pmol/min/$10^6$ cells for taurine.

Membrane transport systems are specific to each of these molecules and depend on $Na^+$ level, temperature, and energy.

The blood biodistribution of TauCl and taurine induce a ready take up by cells of liver, lung, spleen, stomach, intestine and kidneys. In addition, cells present within an inflammatory site readily take up these two molecules (with a inflammation/ blood ratio equal to 6.43 and 4.84 respectively) (Kim C. et al., 1998). Others data show a ready take up by kidneys, liver, spleen, and marrow. The take up by heart and muscle is slow (Huxtable R J, J. Nutr. 1981; 111:1275-86).

e. Antiseptic Properties.

Sodium hypochlorite is a very strong and efficient bactericidal, virucidal and fungicidal agent (Shih et al., 1970; Bloomfield & Miles, 1979, Harrison & Hand, 1980). The bactericidal minimum concentration of NaOCl (i.e. for Gram− and Gram+ bacteria) is 3.36 mM (0.025%) (Heggers J. P. et al., 1991) and the minimum virucidal concentration for VIH is 19.062 mM (1%) of available chlorine.

In contrast, TauCl has a very low bactericidal activity. Only dichloramines generate some bactericidal activity (i.e. with *E. Coli* in acidic conditions) (Marcinkiewicz J. et al., 2000).

3. Inflammation.

Inflammation is a defense mechanism toward all aggression types. Sentinel cells (e.g. macrophages and dendritic cells (DC)), that generate an immune system initialization via both a generation and a release of mediators detect an aggressor (Marcinkiewicz J. et al., 1999). These mediators induce a reaction cascade and both activate and regulate the immune system in an adaptive manner to the aggression type. After the aggressor agents are removed, a regulatory system generates an inflammation turnover followed by a healing/regeneration process.

Two immunity types are perceived: innate (natural) and acquired (adaptive).

The cell part of the innate (natural) immunity is made up of monocytes (mononuclear phagocytes), polymorphonuclear neutrophils (PMN), and natural killer cells (NK). These cells use the complement cascade, or some recognition protein, e.g., reactive protein C and amyloid protein. These proteins are able to attach themselves to carbohydrate molecules present on bacteria membranes. PMNs are included in the first mammalian defense line and cooperate closely with macrophages (one of the major effector cells of the immune system). PMNs are responsible for the non-specific defense in acute inflammation and macrophages take a similar role in both acute and chronic inflammations (Marcinkiewicz J. et al., 1994).

The acquired (adaptive) immunity involves several T cell types and uses antibodies as effector proteins. T cell receptors and antibodies are recognition molecules. B cells recognize carbohydrates, proteins, and some simple chemical structures while T cells recognize only peptides.

Dendritic cells (DC) play an important role. Under inflammatory mediator action, DCs migrate from non-lymphoid tissues to lymphoid organs where they lose their ability to scavenge antigens and acquire an increasing ability to stimulate T cells (Marcinkiewicz J. et al., 1994).

4. Inflammatory Mediators.

Cytokines are the most important intercellular messenger molecules of the immune system (Megarbane B. et al., 1998). Cytokines are generated and released from activated immune cells and they induce some particular biological activities after binding to a specific target cell receptor, in an autocrine or a paracrine manner. Macrophages and T cells are main productive cells of cytokines, although many other cells also can produce them. Cytokines are main and real regulators of both humoral and cellular immune response. Cytokines travel together and the balance of their activities is crucial for immune system regulation, e.g., via a competition between TH1 (IL-2, INF-γ, TNF-β and IL-12) and TH2 (IL-4, IL-5, IL-10 and IL-13) T cells.

TH1 cells are involved in cell immunity and are responsible for cytotoxic activities of macrophage, T cells and natural killer cells.

TH2 cells are associated with humoral response, and, for example, IL-10 (i.e. a TH2 type cytokine) strongly inhibits effective functions of macrophages and TH1 cells (Marcinkiewicz J., 1997).

Cytokine regulatory functions can be extended to a selection of immunoglobulin isotypes during humoral response. Thus, selective inhibitions of cytokines generate an immune response modulation.

Eicosanoids (prostaglandins and leukotrienes) and nitric oxide (NO), produced by activated macrophages, have an important role in the regulation of cytokine production. Eicosanoids are generated from arachidonic acid, which is derived from cell membrane phospholipids.

Prostaglandines (PG) are generated under the cyclooxygenase (COX) catalyzing action. Two cyclooxygenase types are distinguished: the constitutive form (COX1) and the induced form (COX2). COX2 production is activated within inflammatory cells by pro-inflammatory mediators. Thus, COX2 catalyzes the synthesis of prostaglandins $E_2$ (PGE$_2$) and prostacyclins $I_2$ (PGI$_2$) in macrophages, and prostaglandines $D_2$ in mast cells.

Prostaglandins (particularly PGE$_2$) and leukotrienes (particularly LTB$_4$) change immune responses. Therefore, equilibrium in both production and effects of these eicosanoids is needed to induce a harmonious functioning of the immune system.

Nitric oxide (NO) is synthesized from L-arginine under the catalyzing action of the constitutive nitric oxide synthetase ((cNOS) that is calcium dependent) or the induced nitric oxide synthetase ((iNOS) that is calcium independent).

cNOS permits the synthesis of the basic form of nitric oxide (NO) in cells of both endothelium and nervous system.

iNOS is found in a variety of cells including macrophages, neutrophils and hepatocytes. NO generation plays an important role in macrophage cytotoxicity and their ability to kill pathogen microorganisms and, consequently, in mammalian non-specific defense against many pathogens and tumor cells.

More characteristics of these inflammatory mediators are described in Knight J A et al., 2000; Marcinkiewicz J. et al., 1997; and Megarbane B et al., 1998.

5. The Influence of Hypochlorous Acid and Taurine N-Chloramine on an Inflammatory Site.

On Bacteria.

Rat peritoneal macrophages stimulated by non-chlorinated Gram+ bacteria (*Staphylococcus aureus, S. epidermidis*, and *Escherichia coli*) release high concentrations of nitric oxide, TNF-α, and IL-6. The same bacteria chlorinated by HOCl lose their abilities to induce a nitric oxide and TNF-α release while IL-6 production and phagocytosis are not altered (Marcinkiewicz J. et al., 1994).

On Endothelium.

HOCl increases the endothelium permeability and promote leukocyte adherence to microcirculation endothelium. Taurine N-chloramine reduces an endothelium permeability increase generated by PMN activities. Taurine alone is without effect (Tatsumi & Flies, 1994).

On Cellular Growth.

In vitro, on endothelial cells of the human umbilical vein, a HOCl down level (5 nM/$1.2 \times 10^5$ cells) does not induce a cell death but a temporary stop of cell growth (Vissers M C et al., 1999). In addition, low concentrations of both HOCl and physiological chloramines lead in vitro to an inhibition of DNA synthesis and cell division on skin fibroblasts (Vile G F et al., 2000).

On Non-Free Proteins (e.g. Collagen, etc.).

HOCl is a very strong oxidant. In addition, HOCl chlorinates proteins and makes them more vulnerable to an endopeptidase-degradation. Thus, HOCl contributes to a destruction of the tissue surrounding the inflammatory site. TauCl is an oxidant with lower strength and seems to have a lesser responsibility for damage to these tissues.

On Collagenases.

TauCl induces a direct inhibition/inactivation of collagenases while it has no effect on the collagen proteolytic susceptibility. In comparison, leucine and alanine N-monochloramines have no inhibitory effect on collagenases and increase the proteolytic susceptibility of collagen (Davies J M S et al., 1994).

On Free Proteins (Ovalbumin, Bacterial Enzymes, etc.).

Free protein chlorination enhances their immune sensitivity, likely via an improvement of both their treatment and presentation by antigen-presenting cells (i.e. macrophages and dendritic cells). This chlorination is ten times more important for HOCl than taurine-N-monochloramines (TauCl) but, in vivo, TauCl is more stable and, consequently, TauCl can be regarded as the main physiological chlorinating agent (Marcinkiewicz J. et al., 1999).

On Dendritic Cells (DC) (Marcinkiewicz J. et al., 1999).

Two hours pre-incubated rat DCs with TauCl underwent a concentration-dependent inhibitory activity. Thus, a TauCl concentration equal to 500 µM ((TauCl)=500 µM) almost completely inhibits the DC release of reactive oxygen agents (ROS) generated via a respiratory burst, nitric oxide, $PGE_2$, TNF-α, IL-6, IL-10, and IL-12. In addition, the lipopolyssacharide-induced expression of MHC type II and molecule B7-2 is also inhibited. At this concentration, TauCl may be toxic to DC when they are exposed for a long time. With (TauCl)=250 µM, TauCl has a more selective action. Therefore, it inhibits the production of IL-10, IL-12, $PGE_2$, and nitric oxide. TNF-α and ROS generation is not inhibited. In addition, a DC exposition to TauCl seems to promote a TH1 response and decreases the TH2 activity.

On T Cells.

TauCl inhibits the release of IL-2 and IL-6 by T cells pre-incubated with a (TauCl)=100-300 µM and stimulated with either a mitogen, an antigen or an ovalbumin-APC complex (Marcinkiewicz J. et al., 1998).

On Phagocytes.

Antigens chlorinated by HOCl or TauCl do not induce an production of inflammatory mediators by the phagocytes that phagocytosed these antigens (Marcinkiewicz J. et al., 1994 & 1997).

On Macrophages.

Chloramines such as taurine N-mono and (N,N)-dichloramine, N-monochloro-ethanolamine and N-dichlorophosphoethanolamine as well as NaOCl (sodium hypochlorite), all inhibited the release of nitric oxide in a dose-dependent manner. Serine N-chloramine (SerCl) had a lesser half-life than TauCl (immediately after its preparation, (SerCl)=300 µM inhibited the nitric oxide generation for 85%; after 24 hours, this inhibition was reduced to 22%). TauCl inhibited the oxide nitric generation for 98% with (TauCl)=600 µM and 8-22% with (TauCl)=100 µM (i.e., this value changes with cell type). This inhibitory effect was executed within the iNOS gene transcription. Taurine alone was without effect (Marcinkiewicz J. et al., 1995). HOCl (likely via TauCl activity) and TauCl inhibited COX2 post-transcriptional expression i.e. four-hours delay on the kinetic expression of mRNA (and consequently the $PGE_2$ production) and TNF-α transcriptional velocity (i.e., in a dose-dependent manner with an $IC_{60}$=400 µM)(Quinn M R et al., 1996). TauCl inhibits COX2 expression either in non-stimulated and INF-γ-stimulated macrophages. In contrast, in INF-γ-stimulated macrophages TauCl inhibits both the iNOS expression and the production of TNF-α and IL-6. TauCl had no effect on IL-1α production for all stimulation levels. The native taurine alone had no effect on cytokine production. In addition, HOCl-oxidized plasma lipoproteins had an ability to reduce iNOS mRNA synthesis and, thus, to inhibit the nitric oxide production and contribute to atherosclerotic lesion development (Moeslinger T et al., 2000).

On Polymorphonuclear Neutrophils.

TauCl inhibits production of nitric oxide, $PGE_2$, IL-6 and TNF-α in a dose-dependent manner. Native taurine has no effect. Some experiments (Marcinkiewicz J et al., 1998 & 2000) with luminol chemiluminescence-dependent (LCL) measures have shown the following:

Both taurine and TauCl reduced ROS production. However, only high taurine concentrations altered LCL and taurine activity is lower than TauCl.

HOCl reduces myeloperoxidase activity in a retroactive dose-dependent manner. In vitro, TauCl and HOCl inhibit myeloperoxidase extracted from neutrophils.

HOCl (250 µM) inhibits hydrogen peroxide production in a dose-dependent manner. Taurine (500 µM) or nitrite (250 µM) neutralizes this inhibition. TauCl has no effect on this production.

HOCl and TauCl induce a chemiluminescence dose-dependent decrease, TauCl ($IC_{50}$=550 µM) is less efficient than HOCl ($IC_{50}$=100 µM).

TauCl and taurine inhibit superoxide anion ($O_2^-$) production by stimulated neutrophils. This inhibition involves a different mechanism than those implicated in TauCl formation (i.e., association of the taurine (or TauCl) with a myeloperoxydase specific inhibitor generates a synergic effect).

However, high concentrations of taurine alter LCL. This activity is less important than TauCl (Marcinkiewicz J et al., 1998).

On Polymorphonuclear Eosinophils.

HOCl inactivates sulfidopeptide LTC4 sulfoxides and 6-trans-LTB4 leukotrienes only in an extracellular environment (Owen W F et al., 1987).

On Rat Glioma Cells C6.

In the central nervous system of activated glioma cells, TauCl inhibits production of monocyte chemoattractant protein-1 (MCP-1) and macrophage inflammatory protein-2 (MIP-2) both in dose-dependent and post-transcriptional manners (Liu Y et al., 1999). In addition, TauCl inhibits both the iNOS gene transcriptional expression (i.e., nitric oxide production) and the COX2 expression (i.e., $PGE_2$ production) via a post-transcriptional mechanism (Liu Y et al., 1998).

On Fibroblasts.

In rheumatoid arthritis patients, TauCl inhibits fibroblast-like synoviocyte proliferation and decreases the activity of major transcriptional factors of both IL-6 ($IC_{50}$~225 µM) and IL-8 ($IC_{50}$~450 µM) in a dose-dependent manner. Thus, TauCl reduces both IL-6 proinflammatory action and immune cell ability to migrate within an inflammatory site (via an IL-8 inhibition). Whereas IL-6 inhibition is independent of the fibroblast stimulating agent used (e.g. TNF-α, IL-1β or IL-17), IL-8 inhibition is dependent on the stimulation via TNF-α or IL-1β, but not via IL-17. This shows different signaling pathways from TNF-α/IL-1β and IL-17 triggered-transduction (Kontny E et al., 1999). These signaling pathways are dependent on two transcription factors: NF-κB and AP-1. In addition, TauCl inhibits both spontaneous and bFGF-stimulated synoviocyte proliferation (Kontny E et al., 2000).

Low levels of both HOCl and physiological chloramines ($NH_2Cl$, TauCl and N-chlorinated α-amino acid) inhibit both DNA synthesis and cell division of cultured human skin fibroblasts (Vile G L et al., 2000).

On Transcription Factors NF-κB and AP-1.

NF-κB-dependent gene expression may be altered by TauCl activity. In IL-1β-stimulated human synoviocytes, transduction TauCl-inhibition of IL-6 and IL-8 is executed via a DNA-bonding ability reduction of NF-κB and AP-1. IL-6 transcription is under a NF-κB control, while both NF-κB and AP-1 control IL-8 transcription. Thus, a (TauCl)=250 µM selectively reduces the DNA-bonding of NF-κB (i.e., the IL-6 transcription) without altering AP-1 DNA-bonding (i.e., the IL-8 transcription). TauCl acts on both NF-κB and AP-1 transcription factors to inhibit the IL-6 and IL-8 transduction. At 500 μM, TauCl decreases the DNA-bonding activity of both NF-κB and AP-1 (i.e., the transcription of IL-6 and IL-8 is reduced)(Kontny E et al., 2000). These two transcription factors are regulated via a redox mechanism ((Sen C. K., Packer L., Fased J. 1996; 10:709-20), (Li N. & Karin M., Fased J. 1999; 13:1137-43), (Kunsch C. & Medford R. M., Circ Res. 1999 Oct. 15; 85(8):753-66.)). It seems that TauCl may interfere the intracellular redox status of these transcription factors and, therefore, some anti-inflammatory properties may be suggested from TauCl (Kontny E et al., 2000).

On Complement.

The $C_5$ component of the human complement may be activated by oxidants, e.g., hydroxyl radicals, hypochlorite or chloramines (i.e., TauCl and mainly $NH_2Cl$). This activation is due to a $C_5$ structural change induced by a Met. residue oxidation within the $C_5$ protein without peptide cleavage. These changes lead to a $C_6$ bonding site expression, which normally is formed after a $C_5$ specific cleavage in $C_{5a}$ and $C_{5b}$, via one of two $C_3/C_5$ convertases. The $C_5$-oxidation product is similar to $C_{5B}$. Thus, it is able to initiate the combination of the $C_{5-9}$ membrano-lytic complex.

Chemotactic fragments are not directly generated, but activated $C_5$ components (like $C_{5b}$) are readily attacked by enzymes such as kallikrein, which produce $C_{5a}$-like fragments that have a chemotactic activity. It is likely that the $C_{567}$ complex generated with $C_5$ also have a chemotactic activity (i.e., similarly to $C_{5b67}$ complex). In addition, the $C_{5b-9}$ complex is known to stimulate PMNs at non-toxic concentrations. Thus, the same property may be suggested for the corresponding $C_{5-9}$ complex and, consequently, this may lead to a vicious circle that increases tissue lesions (Vogt W, 1996).

SUMMARY

I provide a pharmaceutical composition including at least one halogenated compound, and at least one N-halogenated derivative of at least one compound selected from zwitterionic and/or amino acid compounds, where the composition does not generate substantial stimulation of myeloperoxidase activity in a mammal.

I also provide a method of preparing a pharmaceutical composition including mixing at least one halogenated compound and at least one zwitterionic compound and/or at least one amino acid or their derivatives, and optionally at least one excipient to obtain at least one N-halogenated derivative, and at least one halogenated compound in a sufficient therapeutic amount to not substantially stimulate myeloperoxidase activity in a mammal.

I further provide a method for treatment and/or preventing viral infections, and/or bacterial infections, and/or parasitical infections and/or fungal infections and/or diseases generated from non-conventional transmissible agents, in humans or animals including administering to a human or animal a pharmaceutically effective amount of a pharmaceutical composition including at least one halogenated compound, and at least one N-halogenated derivative of at least one compound selected from zwitterionic compounds and/or the amino acids or their derivatives without substantial stimulation or myeloperoxidase activity in the human or animal.

I still further provide a method of stimulating tissue healing in humans or animals including administering to a human or animal suffering from lesions and infections linked to chronic and/or acute periodontitis a pharmaceutically effective amount of a pharmaceutical composition including (i) at least one sodium halopohalite, and (ii) at least one N-haloamine taurine, wherein halogens from the (i) at least one sodium halopohalite and from the (ii) at least one N-haloamine taurine, which may be the same or different, are selected from the group consisting of fluorine, iodine, bromine and chlorine.

DETAILED DESCRIPTION

I have discovered that in inflammatory sites, beyond any bactericidal activity, NaOCl contributes to (1) an increase in the transition to the cleansing of necrotic and suppurating mass, (2) stimulates local immunity and (3) activates the tissue regeneration process. These abilities are induced from sodium hypochlorite (i.e., hypochlorous acid (HOCl) properties and the hydrolysis generated from sodium hydroxide (NaOH)) and its N-chlorinated derivatives.

Consequently, I provide a pharmaceutical composition comprising (i) at least one halogenated compound and (ii) at least one N-halogenated derivative of at least one compound selected from zwitterionic and/or amino acid compounds.

Within compositions, the halogenated compound (i) is an antiseptic.

Amino acids included in the constitution of compositions can be natural amino acids, derivatives or analogous of the latter.

More particularly, the halogen of the (i) halogenated compounds and the (ii) N-halogenated derivatives of the composition, similar or different, may be fluorine, iodine, bromine, and mainly chlorine.

Favorably, the halogenated compound (i) is an alkaline metal hypochlorite, and preferably the sodium hypochlorite, and the N-halogenated derivative (ii) is an N-halogen derivative of taurine and preferably a taurine N-halo-amine and even more preferably taurine N-chloramine.

The composition is remarkable from its robust properties such as large spectrum of application such as anti-inflammatory, immunity modulation, and tissue healing stimulation as well as those without stimulation of myeloperoxidase activity.

The hypochlorite titer of the composition is preferably below or equal to about 1 mole/liter of available chlorine, and can be adapted to clinical use. Usefully, the composition contains a hypochlorite of alkaline metal. Preferably, the composition contains a sodium hypochlorite q.s. with a minimum titer of available chlorine that is greater than or equal to about 1 picomole/liter.

The N-chloramine titer of the composition is preferably less than or equal to abut 5 moles/liter, and may be adapted to clinical use. Usefully, the composition contains an N-halogenated derivative, such as the taurine N-chloramine, with a concentration between about 5 moles/liter and about 0.01 femtomoles/liter. Preferably, the composition contains a N-halogenated derivative such as the taurine N-chloramine, q.s. with a minimum titer greater than or equal to about 0.01 femtomoles/liter.

The (i) halogenated compound and the (ii) N-halogenated derivative are associated in the composition with an excipient, such as purified water, in accordance with therapeutic use. Preferably, it concerns an osmotic (isotonic) purified water. This excipient may contain diverse agents, pharmaceutically compatible with both (i) the halogenated compound and (ii) the N-halogenated derivative, and which can allow for modification of some physicochemical properties such as stability, pH, pKa, density, solubility, viscosity, coloring, water/ectanol sharing factor, and surface-active, oxidative, olfactory, or gustatory properties of the composition via a suitable agent addition. The composition may also contain some anti-oxidants and/or amino acids that have a dilution effect via neutralization of some alkaline metal hypochlorite molecules. These anti-oxidants, amino acids and their N-halogenated derivatives should have a neutral pharmacological activity or its activity should be pointed to therapeutic aims and should not exercise a direct stimulation of myeloperoxidase activity in the presence of composition active agents.

This disclosure also concerns the preparation of the composition described above. Thus, this composition can be sold in a form to prepare before use, i.e., (i) the halogenated compound(s) can be mixed with (ii) the N-halogenated derivative(s) and one or several excipients. This presentation form can be considered if it is required to guarantee the best time stability of the composition and, in particular, the active agents that constitute the latter. However, even in a presentation where the constituting products would be associated, the composition can be sold with an excipient, such as purified water according to the therapeutic use. Preferably, this should be an osmotic (isotonic) purified water. In addition, this excipient may contain diverse agents pharmaceutically compatible with the totality of final composition molecules, which allow for the modification of some physicochemical properties of the composition via an addition of suitable agent(s) such as stability, pH, pKa, density, solubility, viscosity, coloring, water/ectanol sharing factor, and surface-active, oxidative, olfactory, or gustatory properties.

The composition can also be prepared before its administering to the patient via a mixture comprising:
(i) at least one halogenated compound, and
(ii) at least one N-halogenated derivative of at least one compound selected from zwitterionic and/or amino acid compounds, and their derivatives.

More particularly, the halogen(s) of the halogenated compound (i) and the N-halogenated derivative (ii) may be selected from fluorine, iodine, bromine, and/or chlorine, most preferably chlorine.

Favorably, the halogenated compound (i) is a halide such as an alkaline metal hypochlorite, and preferably the sodium hypochlorite, and the N-halogenated derivative (ii) is a taurine N-halogenated derivative and preferably a taurine N-haloamine and even more preferably the taurine N-chloramine.

The aforementioned halogenated compound(s) (i) are usefully displayed in a liquid or semi-liquid (such as a gel) solution form, favorably within an excipient as described below. These solutions, advantageously hypochlorite solutions, may be stabilized in accordance with the patent EP 0 471 129 A1 via a pH regulatory agent to generate a pH between 10 and 10.5 with respect to cell viability.

The aforementioned N-halogenated derivative(s) (ii) are usefully displayed in a liquid or a semi-liquid (such as a gel) solution form, favorably within an excipient as described below.

Favorably, the composition may be prepared via a mixture of the two solutions described above with at least one excipient according to therapeutic use such as purified water. It preferably contains the osmotic (isotonic) purified water. In addition, this excipient can contain diverse agents, pharmaceutically compatible with all molecules of the final mixing to modify some physicochemical properties of the composition such as stability, pH, pKa, density, solubility, viscosity, coloring, water/ectanol sharing factor, and surface-active, oxidative, olfactory, or gustatory properties via an addition of suitable agent(s).

In addition to the process described above, the composition may be prepared via a mixture of the two following solutions:
(i) at least one halogenated compound as defined above, which is usefully displayed in a liquid or a semi-liquid (such as a gel) solution form, preferably within an excipient as described above,
(iii) at least one zwitterionic compound and/or at least one amino acid and/or at least one primary or secondary amine, (the zwitterionic compound and/or amino acid and/or primary or secondary amino amine are later referred to as "Zw/Aam"), which is usefully displayed in a liquid or a semi-liquid (such as a gel) solution form, favorably within an excipient as described above,
to obtain an association of both (i) at least one halogenated compound and (ii) at least one N-halogenated derivative, and this with a sufficient therapeutic amount of molecules to inhibit myeloperoxidase activity.

This mixture is preferably realized with an excipient as defined above.

In case Zw/Aam is an amino acid, it preferably concerns taurine or a taurine pharmaceutical analog.

In this realization method, when the antiseptic halogenated compound (i) is a halide such as alkaline metal hypochlorite (which is an alkaline metal salt of hypochlorous acid), derivatives generated will be N-chlorinated, and these will more particularly be N-chloramines.

The hypochlorite titer of the first active solution (i) should take into consideration the stoichimetry and reactivity level of the reaction between hypochlorous acid and Zw/Aam molecules. In case this reaction is not complete, remaining Zw/Aam molecules should not stimulate myeloperoxidase activity in the presence of composition active agents.

In case the stoichimetry is 1/1 and with a complete reaction (e.g., between hypochlorous acid and taurine), the hypochlorite titer of the first active solution is preferably lower than or equal to about 6 moles/liter of available chlorine, and must be adapted both to the Zw/Aam molecule amount of the second solution and to clinical status. In this preparation method, the halide solution (i) favorably contains an alkaline metal hypochlorite. Even more preferably, the haloid solution (i) contains sodium hypochlorite q.s. with an available chlorine titer between abut 6 moles/liter and about 1,000.01 femtomoles/liter. The taurine titer of the second solution (iii) of this preparation method is preferably lower than or equal to about 1 moles/liter and may be adapted to clinical use. It is useful for the second solution (iii) of this preparation method to have a taurine concentration between about 5 moles/liter and about 0.01 femtomole/liter. Even more preferably, the second solution (iii) of this preparation method has a taurine titer greater than or equal to about 0.01 femtomole/liter.

The excipient(s) preferably added in methods described above may be used as a secondary diluting solution with the aim to adapt the treatment to the clinical status. It usefully concerns osmotic (isotonic) purified water. This excipient will favorably be similar to the excipient used for the compounds and derivatives that have been mixed, and if they are not identical, the excipient should be pharmaceutically compatible to be mixed with the other excipient(s), before all clinical uses. In addition, this excipient can contain diverse agents, pharmaceutically compatible with all molecules of the final therapeutic mixture with the object of modifying some physicochemical properties of the composition such as stability, pH, pKa, density, solubility, viscosity, coloring, water/ectanol sharing factor, and surface-active, oxidative, olfactory, or gustatory properties via an addition of a suitable agent(s).

This excipient may contain anti-oxidants and/or amino acids that will have both a dilution effect and an oxidant neutralization of the active solution (i) (e.g., the alkaline metal hypochlorite). These anti-oxidants, amino acids and their halogenated derivatives should have a neutral pharmaceutical activity or a pharmaceutical activity inducing the desired therapeutic effect. In all cases they should be both less toxic than the oxidants of (i) the main active solution and pharmaceutically compatible with all molecules of the final therapeutic solution.

The composition can also be sold in a form adapted to local use, e.g., a gel or an aerosol.

The above-mentioned composition is particularly useful in humans or animals for treatments of viral infections and/or bacterial infections and/or parasitical infections and/or fungal infections and/or diseases generated from non-conventional transmissible agents; and/or for treatments of chronic, progressive or acute inflammation; and/or for immunity modulator treatments; and/or for tissue regeneration stimulator treatments. In addition, the therapeutic composition may be used in pre-surgical irrigations and/or per-surgical irrigations and/or post-surgical irrigations.

This disclosure concerns particularly the local treatment of infections due to herpesviridiae family virus.

The composition is preferably used locally aiming to remove secondary effects, e.g., atherosclerosis. It can be applied to all external or internal mucous (e.g., oral, genital, vaginal, ophthalmic, otic, sinusal, nose-and-throat, dermal, and the like). The composition may appear under an adapted form for this administration, such as in a semi-liquid form (e.g., a gel) via an addition of one or several compatible pharmaceutical substances e.g., cellulose, amino acids, peptides, and/or proteins.

The composition may also be adapted to clinical status and/or injured mucous. This adaptation is executed via a concentration change of active products of the therapeutic solutions.

For non-restrictive examples of such adapted therapeutic solutions:

i) For an Infection Treatment.

For endodontic treatment, concentrations between about 1 and about 0.2 moles/liter of sodium hypochlorite, and approximately between about 100 to about 0.001 picomoles/liter of TauCl are preferred (i.e., these concentrations vary with organic matter amount present in canals).

With highly stained keratinized mucous (with profuse presence of organic matter (infectious agents, blood, profuse and varying secretions, suppurating discharge, etc.)), a sodium hypochlorite concentration between about 0.1 and about 0.02 mole/liter and a TauCl concentration between about 1 and about 0.001 picomoles/liter are preferable (non-restricting example).

With moderately stained keratinized mucous (with some organic matter visible on a compress after a gentle friction, for example), a sodium hypochlorite concentration between about 20 and about 10 millimoles/liter of available chlorine and a TauCl concentration between about 1 and about 0.01 nanomole/liter are preferable (non-restricting example).

With clean keratinized mucous (without organic matter visible), preferred concentrations may be between about 10 and about 2 millimoles/liter of available chlorine for sodium hypochlorite (NaOCl), and between about 50 and about 1 micromoles/liter for TauCl (non-restricting example).

With highly stained non-keratinized mucous, concentrations may be between about 50 and about 10 millimoles/liter of available chlorine for NaOCl and between about 0.1 and about 0.001 picomoles/liter for TauCl (non-restricting example).

With moderately stained non-keratinized mucous, concentrations may be between about 10 and about 5 millimoles/liter of available chlorine for NaOCl and between about 1 and about 0.01 nanomoles/liter for TauCl (non-restricting example).

With clean non-keratinized mucous, concentrations may be between about 5 and about 0.8 millimoles/liter of available chlorine for NaOCl and approximately between about 50 and about 1 micromoles/liter for TauCl (non-restricting example).

With important and sensible organs (eyes), concentrations must both be the least toxic (via a high dilution or a specific scavenge of NaOCl by an antioxidant addition) and executed with a profuse diluted irrigation:

For stained organs, concentrations may be between about 5 and about 0.1 millimoles/liter of available chlorine for NaOCl and between about 1 and about 0.01 femtomoles/liter for TauCl (non-restricting example).

For non-stained organs, concentrations may be between about 0.1 and about 0.01 millimoles/liter of available chlorine for NaOCl and between about 50 and about 1 micromoles/liter for TauCl (non-restricting example).

ii) For the treatment of non-stained organs with the object of immune stimulation and/or tissue regeneration, concentrations could be between about 500 and about 1 micromoles/liter of available chlorine for NaOCl and between about 200 and about 10 micromoles for TauCl (non-restricting example).

The composition is useful for local treatment of diseases or inflammatory processes that can be chronic, and/or progressive and/or acute. The composition is also recommended for pre-surgical irrigation and/or per-surgical irrigation and/or post-surgical irrigation of internal and/or external mucous and of opened-injures. This disclosure more particularly concerns a treatment method of lesions and infections described above, which comprises contacting the composition on mucous that must be treated, (for non-restricting example) between 2 and 3 times a day and approximately during 20 to 60 seconds, not followed by a rinsing. The composition amount employed should be sufficient to not generate a total neutralization of the therapeutic active agents. In the therapeutic use, the solution should not stay static. Concentrations of the composition should be adapted to the evolution of the clinical status until healing.

This disclosure more particularly concerns the local treatment of lesions and infections linked to chronic and/or acute parodontitis. Thus, the composition is usefully adapted for irrigation of periodontal pockets, with the aim for removing these periodontal pockets as the composition has both antiseptic and anti-inflammatory activities, and acts as an immunity modulator and healing stimulator of periodontal tissues (i.e., alveolar bone, alveolodental ligament and gingiva).

Chronic periodontitis is a disease mainly due to pathologic action of anaerobic bacteria, and particularly *Actinobacillus actinomycetemcomitans*, *Porphyromonas gingivalis*, *Bacteroides forsythus* and *Prevotella intermedia*. These bacteria induce chronic inflammatory processes that generate a progressive destruction of periodontal tissues (teeth supporting tissue). Periodontitis may result in the removal of bone tissue followed by tooth loss.

Whatever the treatment phase of chronic periodontitis, periodontal pocket irrigations have to be executed in the presence of a strong surgical vacuum extraction with the object of avoiding swallowing or inhalation of the therapeutic solution by the patient.

i) Attack treatment (i.e., between two and three weeks up to the disappearance of bleeding in probing depth of periodontal pockets).

J 1: after an assessment of the clinical status, crevicular spaces (with or without periodontal pockets) of oral cavity teeth should be irrigated. A full mouth followed by a tongue brushing, with a mixed solution of 0.1% chlorhexidine and 0.3% hydrogen peroxide, should be prescribed twice a day (far from the teeth brushing) over ten days, then twice to three times a week ad vitam aeterman (however, in halitosis, the initial attack treatment should be repeated). Two or three appointments should be scheduled.

In the other sessions, the following process will be recommended: education, checking, and motivation for periodontal hygiene; meticulous irrigation (1 ml minimum of the highly stained keratinized mucous solution for each periodontal site); meticulous scaling and root planning.

When all root surfaces are planned and cleaned, a probing session (this consists first of an irrigation followed by a probing depth) should be executed to evaluate the degree of periodontal disease. Some complementary examinations can be made such as sampling picks up and biological examinations.

ii) Primary curative treatment (i.e., four weeks).

Meticulous irrigation of periodontal pockets once every ten days applying the solution for moderately stained keratinized mucous, except for sites with a profuse dental plaque (such as interdental furcations) where the solution for highly stained keratinized mucous should be applied.

At the last session of the primary curative treatment, an irrigation follows probing depth and root planning.

iii) Secondary curative treatment (until clinical removal of the periodontal pockets).

Meticulous irrigation of periodontal pockets once every ten days with the solution for clean keratinized mucous, except for sites with + or − profuse dental plaque (e.g., interdental furcations) where the therapeutic composition for highly or moderate stained keratinized mucous should be used.

Every three sessions of the secondary curative treatment, an irrigation follows probing depth of periodontal pockets and root planning.

iv) Maintenance treatment.

In any diagnostic of clinical healing, a maintenance treatment should be executed. This treatment type is similar to the secondary curative treatment except that appointments should be made once every three weeks.

If after two mouths of treatment a notable healing rather than a recurrence is observed, the last treatment phase—supervision—can be initiated.

In case of recurrence, the treatment should be started again at a stage that depends on the clinical status observed, i.e., the attack treatment, or the primary or the secondary curative treatment.

v) Supervision.

An appointment should be made once every six weeks. A meticulous probing depth will be practiced.

In case of no-recurrence, all crevicular spaces should be irrigated with the solution for moderate stained or clean keratinized mucous, followed by a meticulous root planning.

In case of recurrence, the treatment should be started again at a stage that depends on the clinical status observed (i.e., the attack treatment, or the primary or the secondary curative treatment).

In addition, this disclosure also concerns bone-filling surgical periodontal treatments with some biomaterials associated with the composition and/or one of its components.

BIBLIOGRAPHICAL REFERENCES

The subject matter of the bibliographical references listed below is incorporated by reference.

1. Bloomfield S F, Miles G A.—The antibacterial properties of sodium dichloro-isocyanurate and sodium hypochlorite formulations.—J Appl Bacteriol. 1979 February; 46(1):65-73.
2. Cantin A M.—Taurine modulation of hypochlorous acid-induced lung epithelial cell injury in vitro. Role of anion transport.—J Clin Invest. 1994 February; 93(2):606-14.
3. Davies J M, Horwitz D A, Davies K J.—Inhibition of collagenase activity by N-chlorotaurine, a product of activated neutrophils.—Arthritis Rheum. 1994 March; 37(3):424-7.
4. Grisham M B, Jefferson M M, Melton D F, Thomas E L.—Chlorination of endogenous amines by isolated neutrophils. Ammonia-dependent bactericidal, cytotoxic, and cytolytic activities of the chloramines.—J Biol Chem. 1984 Aug. 25; 259(16):10404-13.
5. Hand R E, Smith M L, Harrison J W.—Analysis of the effect of dilution on the necrotic tissue dissolution property of sodium hypochlorite.—J Endod. 1978 February; 4(2):60-4.
6. Heggers J P, Sazy J A, Stenberg B D, Strock L L, McCauley R L, Herndon D N, Robson M C.—Bactericidal and wound-healing properties of sodium hypochlorite solutions: the 1991 Lindberg Award.—J Burn Care Rehabil. 1991 September-October; 12(5):420-4.
7. Hidalgo E, Dominguez C.—Growth-altering effects of sodium hypochlorite in cultured human dermal fibroblasts.—Life Sci. 2000 Aug. 4; 67(11):1331-44.
8. Huxtable R J—Sources and turnover rates of taurine in nursing and weaned rat pups.—J. Nutr. 1981; 111:1275-86.
9. Kim C, Chung J-K, Jeong J M, Chang Y S, Lee Y J, Kim Y J, Lee M C, Koh C-s, Kim B-K—Uptake of taurine and taurine chloramine in murine macrophages and their distribution in mice with experimental inflammation.—Adv Exp Med Biol. 1998; 442:169-76.
10. Kim C, Park E, Quinn M R, Schuller-Levis G.—The production of superoxide anion and nitric oxide by cultured murine leukocytes and the accumulation of TNF-alpha in the conditioned media is inhibited by taurine chloramine.—Immunopharmacology. 1996 September; 34 (2-3):89-95.
11. Knight J A.—Review:free radicals, antioxidants, and the immune system.—Annals of Clinical laboratory Science. 2000; 30(2):145-58.
12. Kontny E, Grabowska A, Kowalczewski J, Kurowska M, Janicka I, Marcinkiewicz J, Maslinski W.—Taurine chloramine inhibition of cell proliferation and cytokine production by rheumatoid arthritis fibroblast-like synoviocytes.—Arthritis Rheum. 1999 December; 42(12):2552-60.
13. Kontny E, Szczepanska K, Kowalczewski J, Kurowska M, Janicka I, Marcinkiewicz J, Maslinski W.—The mechanism of taurine chloramine inhibition of cytokine (interleukin-6, interleukin-8) production by rheumatoid arthritis fibroblast-like synoviocytes.—Arthritis Rheum. 2000 October; 43(10):2169-77.
14. Kunsch C, Medford R M.—Oxidative stress as a regulator of gene expression in the vasculature.—Circ Res. 1999 Oct. 15; 85(8):753-66.
15. Lelianov A D, Grachev A M, Sergienko V I, Farashchuk N F, Kiriushenkova S V.—[The use of an electrolytic solution of sodium hypochlorite in acute suppurative diseases of the soft tissues].—Klin Khir 1991; (12):16-9. Russian.
16. Liu Y, Schuller-Levis G, Quinn M R.—Monocyte chemoattractant protein-1 and macrophage inflammatory protein-2 production is inhibited by taurine chloramine in rat C6 glioma cells.—Immunol Lett. 1999 Oct. 1; 70(1):9-14.
17. Liu Y et al.—Taurine chloramine inhibits production of nitric oxide and protaglandin E2 in activated C6 glioma cells by suppressing inducible nitric oxide synthase and cyclo-oxygenase-2 expression.—Brain res mol brain res. 1998 Aug. 31; 59(2):189-95.
18. Male D., Champion B., Cooke A.—Advanced immunology.—2$^{nd}$ ed. philadelphia: J.B. Lippincott company; 1989; 5:1-15.
19. Marquez L A, Dunford H B.—Chlorination of taurine by myeloperoxidase. Kinetic evidence for an enzyme-bound intermediate.—J Biol Chem. 1994 Mar. 18; 269(11):7950-6.
20. Marcinkiewicz J, Czajkowska B, Grabowska A, Kasprowicz A, Kociszewska B.—Differential effects of chlorination of bacteria on their capacity to generate NO, TNF-alpha and IL-6 in macrophages.—Immunology. 1994 December; 83(4):611-6.
21. Marcinkiewicz J et Al.—Taurine chloramine, a product of actived neutrophils, inhibits in vitro the generation of nitric oxide and other macrophage inflammatory mediators.—Journal of leukocyte biology. 1995 December; 58: 667-74.
22. Marcinkiewicz J.—Regulation of cytokine production by eicosanoids and nitric oxide.—Arch Immunol Ther Exp (Warsz). 1997; 45 (2-3):163-7.
23. Marcinkiewicz J.—Nitric oxide and antimicrobial activity of reactive oxygen intermediates.—Immunopharmacology. 1997 August; 37(1): 35-41.
24. Marcinkiewicz J.—Neutrophil chloramines: missing links between innate and acquired immunity.—Immunol Today. 1997 December; 18(12):577-80.
25. Marcinkiewicz J, Grabowska A, Bereta J, Bryniarski K, Nowak B.—Taurine chloramine down-regulates the generation of murine neutrophil inflammatory mediators.—Immunopharmacology. 1998 July; 40(1):27-38.
26. Marcinkiewicz J, Grabowska A, Chain B M.—Modulation of antigen-specific T-cell activation in vitro by taurine chloramine.—Immunology. 1998 July; 94(3):325-30.
27. Marcinkiewicz J, Nowak B, Grabowska A, Bobek M, Petrovska L, Chain B.—Regulation of murine dendritic cell functions in vitro by taurine chloramine, a major product of the neutrophil myeloperoxidase-halide system.—Immunology. 1999 November; 98(3):371-8.
28. Marcinkiewicz J, Chain B, Nowak B, Grabowska A, Bryniarski K, Baran J.—Antimicrobial and cytotoxic activity of hypochlorous acid: interactions with taurine and nitrite.—Inflamm Res. 2000 June; 49(6):280-9.
29. Megarbane B, Galanaud P, Emilie D—Cytokines du systeme de defense:interleukines et chimiokines—Médecine Thérapeutique. 1998 October; 4(8):641-53.
30. Moeslinger T, Friedl R, Volf I, Brunner M, Koller E, Spieckermann PG.—Inhibition of inducible nitric oxide synthesis by oxidized lipoprotein (a) in a murine macrophage cell line.—FEBS Lett. 2000 Jul. 28; 478 (1-2):95-9.
31. Owen W F Jr, Soberman R J, Yoshimoto T, Sheffer A L, Lewis R A, Austen K F.—Synthesis and release of leukotriene C4 by human eosinophils. J Immunol.—1987 Jan. 15; 138(2):532-8.
32. Park E, Schuller-Levis G, Jia J H, Quinn M R.—Preactivation exposure of RAW 264.7 cells to taurine chloramine attenuates subsequent production of nitric oxide and expression of iNOS mRNA.—J Leukoc Biol. 1997 February; 61(2):161-6.
33. Park E, Quinn M R, Wright C E, Schuller-Levis G.—Taurine chloramine inhibits the synthesis of nitric oxide and the release of tumor necrosis factor in activated RAW 264.7 cells.—J Leukoc Biol. 1993 August; 54(2):119-24.
34. Pullar J M, Winterbourn C C, Vissers M C.—Loss of GSH and thiol enzymes in endothelial cells exposed to sublethal concentrations of hypochlorous acid.—Am J Physiol. 1999 October; 277 (4 Pt 2):H1505-12.
35. Quinn M R, Park E, Schuller-Levis G.—Taurine chloramine inhibits prostaglandin E2 production in activated RAW 264.7 cells by post-transcriptional effects on inducible cyclo-oxygenase expression.—Immunol Lett. 1996 May; 50(3):185-8.
36. Segura J J, Jimenez-Rubio A, Guerrero J M, Calvo J R.—Comparative effects of two endodontic irrigants, chlorhexidine digluconate and sodium hypochlorite, on macrophage adhesion to plastic surfaces.—J Endod. 1999 April; 25(4):243-6.
37. Sen C K, Packer L.—Antioxidant and redox regulation of gene transcription.—FASEB J. 1996 May; 10(7):709-20.
38. Shih M, Marshall F J, Rosen S.—The bactericidal efficiency of sodium hypochlorite as an endodontic irrigant.—Oral Surg Oral Med Oral Pathol. 1970 April; 29(4):613-9.
39. Tatsumi T, Fliss H.—Hypochlorous acid and chloramines increase endothelial permeability: possible involvement of cellular zinc.—Am J Physiol. 1994 October; 267 (4 Pt 2):H1597-607.
40. The SD.—The solvent action of sodium hypochlorite on fixed and unfixed necrotic tissue.—Oral Surg Oral Med Oral Pathol. 1979 June; 47(6):558-61.
41. Vissers M C, Pullar J M, Hampton M B.—Hypochlorous acid causes caspase activation and apoptosis or growth arrest in human endothelial cells.—Biochem J. 1999 Dec. 1; 344 Pt 2:443-9.
42. Vile G F, Rothwell L A, Kettle A J.—Initiation of rapid, P53-dependent growth arrest in cultured human skin fibroblasts by reactive chlorine species.—Arch Biochem Biophys. 2000 May 1; 377(1):122-8.
43. Vogt W.—Complement activation by myeloperoxidase products released from stimulated human polymorphonuclear leukocytes.—Immunobiology. 1996 August; 195 (3):334-46.
44. Wright C E, Tallan H H, Lin Y Y, Gaull G E.—Taurine: biological update.—Annu Rev Biochem. 1986; 55:427-53.
45. Zgliczynski J M, Stelmaszynska T, Domanski J, Ostrowski W.—Chloramines as intermediates of oxidation reaction of amino acids by myeloperoxidase.—Biochim Biophys Acta. 1971 Jun. 16; 235(3):419-24.

The invention claimed is:
1. A method of:
(a) treating bacterial infections, and
(b) treating chronic, progressive or acute inflammation, and
(c) modulating immunity, and
(d) stimulating tissue healing, in humans or animals, comprising administering to said human or animal suffering from lesions and infections linked to chronic and/or acute periodontitis an effective amount of a pharmaceutical composition comprising:
(i) at least one sodium hypohalite, and
(ii) at least one N-halo-amine taurine,
wherein the halogens from the (i) at least one sodium hypohalite and from the (ii) at least one N-halo-amine taurine, which may be the same or different, are selected from the group consisting of fluorine, iodine, bromine and chlorine, and
wherein said at least one sodium hypohalite and at least one N-halo-amine taurine treats bacterial infections, and treats chronic, progressive or acute inflammation, modulates immunity, and stimulates tissue healing without substantial stimulation of myeloperoxidase activity in said human or animal.

2. The method of claim 1, wherein the halogens from the (i) at least one sodium hypohalite and from the (ii) at least one N-halo-amine taurine, which are the same or different, are selected from the group consisting of fluorine, iodine, and bromine.

3. The method of claim 1, comprising local treatment of lesions and infections linked to chronic and/or acute periodontitis.

4. The method of claim 1, which stimulates periodontal tissues healing.

5. The method of claim 1, comprising irrigation of the periodontal pockets.

6. The method of claim 1, wherein (i) at least one sodium hypohalite has a concentration of more than 0.01 mM and wherein (ii) the N-halo-amine taurine has a concentration of more than 1 µM.

* * * * *